US012788509B2

(12) United States Patent
Wang et al.

(10) Patent No.: US 12,788,509 B2
(45) Date of Patent: Nov. 10, 2026

(54) DRIVE APPARATUS FOR SURGICAL ROBOT, AND SURGICAL ROBOT

(71) Applicant: ROBGENIX MEDICAL PTE. LTD., Singapore (SG)

(72) Inventors: Wenhui Wang, Shanghai City (CN); Hao Chen, Shanghai City (CN); Qianlong Zhang, Shanghai City (CN); Cunwang Ge, Shanghai City (CN); Gang Wu, Shanghai City (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/183,211

(22) Filed: Apr. 18, 2025

(65) Prior Publication Data

US 2026/0053579 A1 Feb. 26, 2026

Related U.S. Application Data

(63) Continuation of application No. PCT/CN2024/140581, filed on Dec. 19, 2024.

(30) Foreign Application Priority Data

Aug. 15, 2024 (CN) ......................... 202421987390.1

(51) Int. Cl.

*B25J 19/00* (2006.01)
*A61B 34/00* (2016.01)
*A61B 34/30* (2016.01)

(52) U.S. Cl.

CPC .............. *A61B 34/30* (2016.02); *A61B 34/74* (2016.02); *A61B 2034/304* (2016.02); *A61B 2034/305* (2016.02)

(58) Field of Classification Search

CPC ... A61B 34/30; A61B 34/74; A61B 2034/304; A61B 2034/305

See application file for complete search history.

(56) References Cited

U.S. PATENT DOCUMENTS

| | | | | |
|---|---|---|---|---|
| 11,751,962 | B1 * | 9/2023 | Yang | A61B 34/74 700/245 |
| 2019/0069960 | A1 * | 3/2019 | Vakharia | B25J 13/006 |

(Continued)

FOREIGN PATENT DOCUMENTS

| | | | |
|---|---|---|---|
| CN | 114193504 | A | 3/2022 |
| CN | 117838301 | A | 4/2024 |

(Continued)

OTHER PUBLICATIONS

International Search Report from PCT/CN2024/140581, dated Apr. 23, 2025, English translation included, pp. 1-13.

(Continued)

*Primary Examiner* — Dalena Tran
(74) *Attorney, Agent, or Firm* — Robert C. Kowert; Kowert, Hood, Munyon, Rankin & Goetzel, P.C.

(57) ABSTRACT

A drive apparatus for surgical robot, and a surgical robot are disclosed, the apparatus comprising an assembly frame, multiple drive motors, at least one driver and a controller; the frame comprising a first frame plate and a second frame plate secured to the first frame plate; each drive motor being mounted on the first frame plate and having a power output end for connecting to and providing driving power for an external device; the driver being mounted on the second frame plate and connected electrically and communicatively to the controller and the drive motors, and being configured to cause the drive motors to output respective powers according to instructions of the controller for providing multiple driving powers for the external device. The surgical robot comprises the apparatus. The drive apparatus enables (Continued)

configuration of multiple drive motors and at least one driver within a surgical robotic actuation device with limited space.

20 Claims, 15 Drawing Sheets

(56) References Cited

U.S. PATENT DOCUMENTS

| | | | | |
|---|---|---|---|---|
| 2020/0205918 | A1 | 7/2020 | Uekaji et al. | |
| 2021/0259792 | A1* | 8/2021 | Hares | A61B 34/30 |
| 2021/0322116 | A1* | 10/2021 | Swayze | B25J 9/102 |
| 2023/0035508 | A1 | 2/2023 | Clark et al. | |

FOREIGN PATENT DOCUMENTS

| | | | |
|---|---|---|---|
| CN | 117883128 | A | 4/2024 |
| CN | 117958973 | A | 5/2024 |
| CN | 220896454 | U | 5/2024 |
| WO | 2017220822 | A1 | 12/2017 |

OTHER PUBLICATIONS

Extended European Search Report from Application No. PCT/CN2024140581, dated Feb. 6, 2026, pp. 1-9.

* cited by examiner

DRIVE APPARATUS FOR SURGICAL ROBOT, AND SURGICAL ROBOT

This application is a continuation of International Application No. PCT/CN2024/140581, filed on Dec. 19, 2024, which claims the priority to Chinese Patent Application No. 202421987390.1 filed on Aug. 15, 2024, and entitled "DRIVE APPARATUS FOR SURGICAL ROBOT, AND SURGICAL ROBOT", the entire disclosure of which is incorporated by reference herein.

TECHNICAL FIELD

The present disclosure relates to the field of medical device technology, and in particular to a drive apparatus for surgical robot, and a surgical robot.

BACKGROUND

Traditional interventional surgeries typically require surgeons to manually operate passive medical devices. In contrast, interventional surgical robots enable remote control of actuation devices for driving the movement of these passive devices, thus not only relieving surgeons from complex and/or physically demanding manual operations so as to allow them to focus entirely on diagnosis and/or decision-making, but also lowering the technical threshold for surgeries and/or reducing radiation exposure to surgeons. However, the actuation device and/or power cabin (drive apparatus) of the interventional surgical robot face limitations due to sterile operating protocols and the confined workspace of passive medical devices, which lead to a highly compact layout of the drive apparatus, resulting in challenges such as intricate cable routing, stringent thermal management requirements, and/or significant electromagnetic interference.

SUMMARY

The present disclosure aims to provide a drive apparatus for surgical robot, and a surgical robot that address the shortcomings of the prior art.

In order to solve the above technical problems, the following technical solutions are provided in the present disclosure.

A drive apparatus for surgical robot is provided, including an assembly frame, a plurality of drive motors, at least one driver and a controller; where the assembly frame includes a first frame plate and a second frame plate that is fixedly connected to the first frame plate; each of the plurality of drive motors is mounted on the first frame plate and has a power output end for connecting to an external device and providing driving power for the external device; the at least one driver is mounted on the second frame plate and connected to electrically and communicatively the controller and the plurality of drive motors, and is configured to cause, according to instructions of the controller, the plurality of drive motors to output respective powers for providing a plurality of driving powers for the external device.

Further, the at least one driver includes a plurality of single-axis drivers, where the number of the single-axis drivers is the same as the number of the drive motors, each of the single-axis drivers being electrically and communicatively connected to one of the drive motors, and the plurality of single-axis drivers being electrically and communicatively connected to each other.

Further, the number of the single-axis drivers and the number of the drive motors are both twelve.

Further, at least one driver includes a first multi-axis driver, a second multi-axis driver, and a third multi-axis driver each electrically and communicatively connected to more than one of the drive motors, where the first multi-axis driver, the second multi-axis driver, and the third multi-axis driver are electrically and communicatively connected to each other.

Further, the first multi-axis driver is electrically and communicatively connected to three of the drive motors, the second multi-axis driver is electrically and communicatively connected to another three of the drive motors, and the third multi-axis driver is electrically and communicatively connected to six of the drive motors.

Further, the first multi-axis driver, the second multi-axis driver, and the third multi-axis driver are disposed within the assembly frame in a three-layer configuration of upper, middle, and lower layers.

Further, the assembly frame includes a third frame plate fixedly connected to the first frame plate and the second frame plate, where the third frame plate has an opening that includes a mechanical arm interface, a power interface, a communication interface and an air convection interface.

Further, the drive apparatus further includes a heat dissipation unit disposed near a peripheral edge within the assembly frame.

Further, the heat dissipation unit includes a cooling fan, a piston air pump, and/or a blower.

Further, a hold key and/or a reset key are provided on the controller.

Further, each of the drive motors is provided with a constant speed mode motion key, a position mode motion key, and/or a constant torque mode motion key.

Further, each of the drive motors is provided with a safety torque off key.

Further, each of the drive motors has an output shaft with an external encoder provided thereon.

Further, the drive apparatus is disposed in a surgical robotic actuation device and connected to a mechanical arm of the surgical robot through a power cable and a communication cable.

A surgical robot includes the aforesaid drive apparatus for surgical robot.

Compared with the prior art, the beneficial effects of the present disclosure are as follows:

1. The drive apparatus for surgical robot according to the present disclosure is provided with an assembly frame, a plurality of drive motors and at least one driver, where the plurality of drive motors and at least one driver are disposed within a limited space defined by the first and second frame plates, thereby enabling the configuration of multiple drive motors and at least one driver within the space-constrained surgical robotic actuation device, thus allowing the actuation device to meet the functional requirements of surgeons for controlling passive medical devices, while ensuring high stability and reliability.
2. The drive apparatus for surgical robot according to the present disclosure is provided with a plurality of drive motors and at least one driver that are disposed closely, thereby preventing cable damage, short circuits, disconnections, communication interruptions and/or excessive cable impedance, thus enhancing the control accuracy of the surgical robot and reducing the risk of failure, while meeting the requirements for wiring, routing, process, maintenance, heat dissipation and electromagnetic interference avoidance.

3. The drive apparatus for surgical robot according to the present disclosure is provided with at least one driver including a plurality of single-axis drivers, that are in one-to-one correspondence and communicate in series with the plurality of drive motors, thereby enabling efficient utilization of the limited space defined by the first and second frame plates and thus lowering space requirements, and enabling precise, rapid and/or reliable surgical operations under the control of the surgical robot. Moreover, in the event of a single-axis driver failure, only the faulty single-axis driver needs to be replaced, ensuring convenience, efficiency, and cost-effectiveness.
4. The drive apparatus for surgical robot according to the present disclosure is provided with at least one driver including first, second, and third multi-axis drivers, each electrically and communicatively connected to more than one drive motor, which can reduce the number of cables and meet actual needs.
5. The drive apparatus for surgical robot according to the present disclosure is provided with a heat dissipation unit, which can improve the heat dissipation effect of the drive apparatus.
6. The drive apparatus for surgical robot according to the present disclosure is provided with a third frame plate with an opening provided thereon and including a power interface, a communication interface and an air convection interface, which achieves a simple structure and ease of use, and can meet actual needs.
7. The drive apparatus for surgical robot according to the present disclosure is provided with an external encoder mounted on the output shaft of the drive motor, which can prevent uncontrolled motor operation (runaway) caused by damage to the original built-in encoder of the motor, and can compensate for the lack of multi-turn feedback function of the original encoder, enabling precise multi-turn control.
8. The drive apparatus for surgical robot according to the present disclosure is provided with a hold key and/or a reset key on the controller, where the hold key causes the device to maintain the current position and record it, and the reset key causes the device to return to its initial position with a single press, thereby enhancing the convenience of using the drive apparatus.
9. The drive apparatus for surgical robot according to the present disclosure is provided with a constant speed mode motion key, a position mode motion key, and/or a constant torque mode motion key on the drive motor, allowing for selection of appropriate motion mode based on actual needs, thus enhancing convenience and efficiency.
10. The drive apparatus for surgical robot according to the present disclosure is provided with a safe torque off button on the drive motor, thereby enabling the immediate shutdown of output torque in emergency situations, thus enhancing the safety of the drive motor operation.
11. The drive apparatus for surgical robot according to the present disclosure achieves high stability, reliability, and safety, and also features a simple structure, ease of use, and a broad application scope.

Other advantages of the present disclosure will be further explained in detail with reference to the following description and drawings.

It should be understood that the above description is merely an overview of the technical solution of the present disclosure, for enabling a general understanding of the technical means and facilitating implementation in accordance with the specification. In order to further clarify the above and other purposes, features and advantages of the present disclosure, the specific implementation of the present disclosure is specifically illustrated below.

BRIEF DESCRIPTION OF THE DRAWINGS

In order to more clearly illustrate the technical solution of the embodiments of the present disclosure, the drawings required for the embodiments will be briefly introduced below. The drawings herein are incorporated into the specification and constitute a part of the specification. These drawings show embodiments that conform to the present disclosure and are used together with the specification to illustrate the technical solution of the present disclosure. It should be understood that the drawings only illustrate certain embodiments of the present disclosure and should not be considered as limiting the scope of protection. A person of ordinary skill in the art can obtain other related drawings based on these drawings without creative effort. In addition, the same reference numerals are used throughout the drawings to represent the same components. In the accompanying drawings.

In the drawings.

Figure 1:
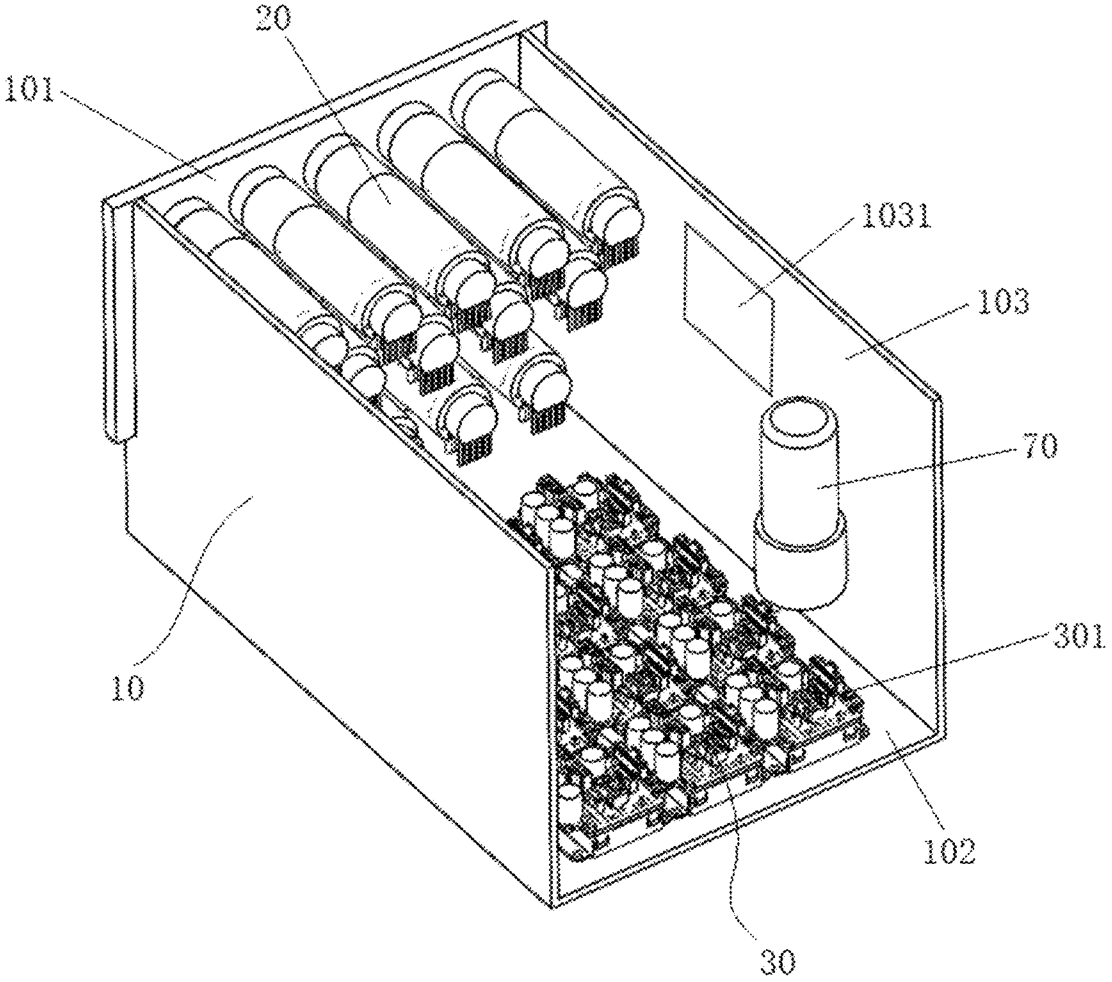
FIG. 1 shows a schematic structural diagram of a specific embodiment of the drive apparatus for surgical robot according to the present disclosure.

10: assembly frame; 101: first frame plate; 102: second frame plate; 103: third frame plate; 1031: opening; 104: bottom shell; 105: top cover; 106: connector hole; 20: drive motor; 201: external encoder; 30: driver; 300: display screen; 301: single-axis driver; 302: first multi-axis driver; 303: second multi-axis driver; 304: third multi-axis driver; 40: outer catheter; 50: middle catheter; 60: inner catheter; 70: heat dissipation unit; 80: motor assembly; 90: transmission cabin; 901: input end connection assembly; 902: chassis assembly; 903: first adapter transmission assembly; 904: second adapter transmission assembly; 905: third adapter transmission assembly; 906: axial end fixing assembly; 100: driver assembly; 110: first adapter assembly; 120: second adapter assembly; 130: third adapter assembly.

DETAILED DESCRIPTION

The present disclosure is further described below with reference to the embodiments shown in the accompanying drawings.

The directional terms such as "inside" and "outside" recited in the present disclosure are only intended to be interpreted with reference to the accompanying drawings. Therefore, these directional terms are intended to be used to explain and understand the present disclosure, rather than to limit its scope.

As shown in FIGS. 1, 2, and 5 to 17, the drive apparatus for surgical robot according to the present disclosure includes an assembly frame 10, a plurality of drive motors 20, at least one driver 30, and a controller.

The assembly frame 10 includes a first frame plate 101 and a second frame plate 102 that is fixedly connected to the first frame plate 101.

Figure 5:
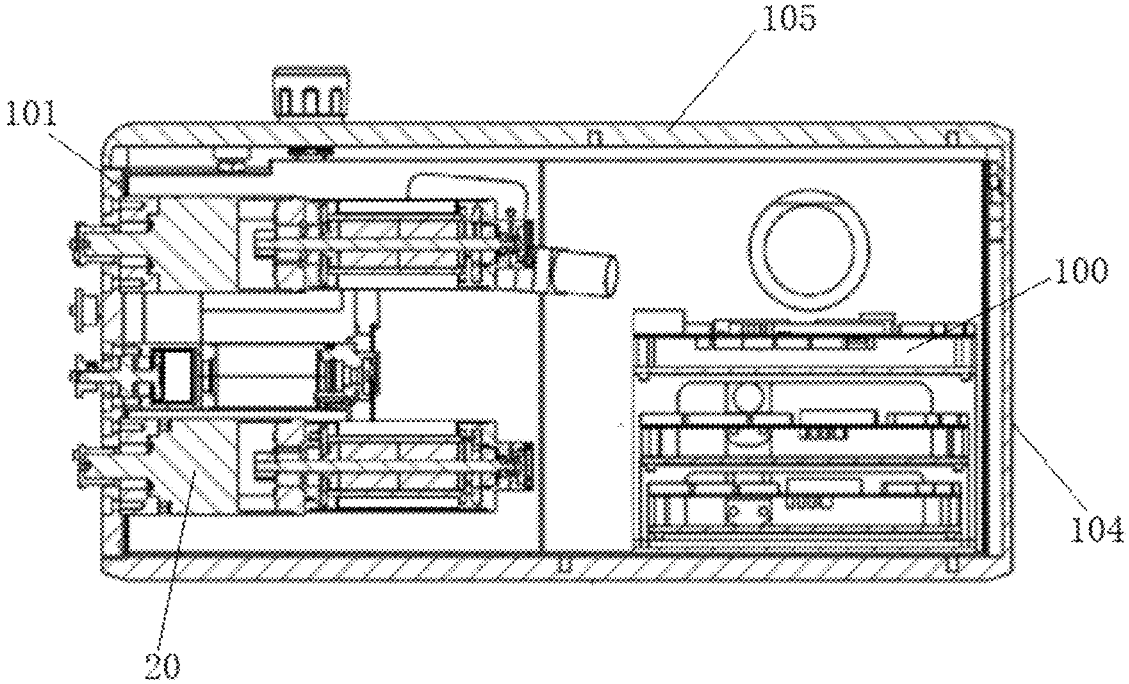
FIG. 5 shows a schematic cross-sectional view of a specific embodiment of the drive apparatus for surgical robot according to the present disclosure.
Figure 6:
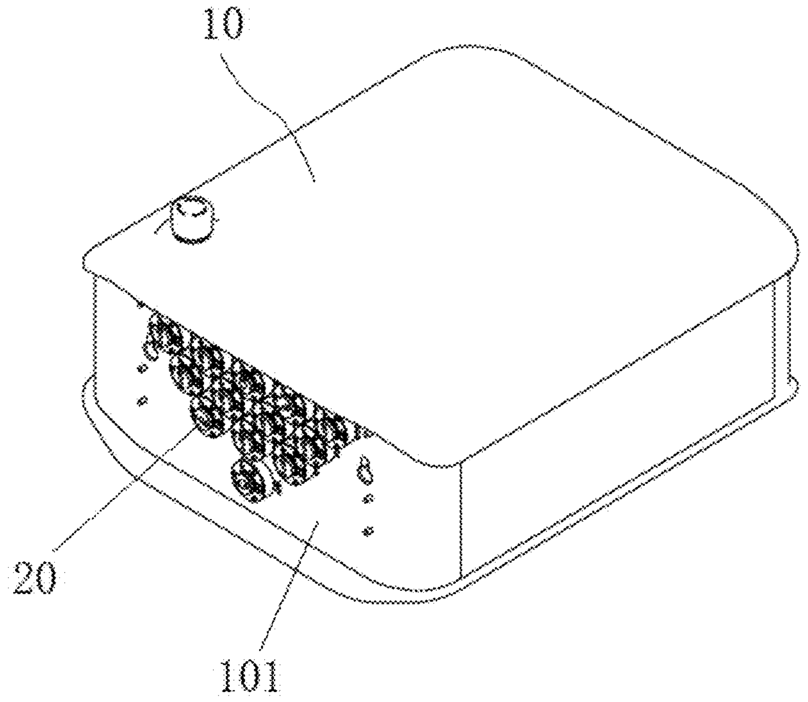
FIG. 6 shows a schematic structural diagram of a specific embodiment of the drive apparatus for surgical robot according to the present disclosure.

Each of the drive motors 20 is mounted on the first frame plate 101 (as shown in FIG. 5). Each drive motor 20 has a power output end that extends outwardly through the first frame plate 101 for connecting to and providing driving power for an external device.

The at least one driver 30 is mounted on the second frame plate 102. The at least one driver 30 is electrically and communicatively connected to the controller and the plurality of drive motors 20. The at least one driver 30 is configured to cause the plurality of drive motors 20 to output respective powers, according to instructions of the controller, thereby providing a plurality of drive powers for the external device.

The at least one driver 30 has an accompanying software program configured to convert the instructions from the controller into control signals recognizable by the plurality of drive motors 20 to cause the plurality of drive motors 20 to output respective powers for providing a plurality of drive powers for the external device. For example, the drive apparatus can provide drive power for the surgical robotic actuation device, and can control the position, speed and/or torque of the surgical robotic actuation device. By mounting the plurality of drive motors 20 on the first frame plate 101 and mounting at least one driver 30 on the second frame plate 102, the plurality of drive motors 20 and the at least one driver 30 can be disposed closely, so that the plurality of drive motors 20 and the at least one driver 30 are disposed within the limited space defined by the first and second frame plates 101 and 102, thereby enabling the configuration of the plurality of drive motors 20 and the at least one driver 30 within the space-constrained surgical robotic actuation device (including the drive apparatus for surgical robot), thus allowing the actuation device to meet the functional requirements of surgeons for operating the passive medical devices, while ensuring high stability and reliability. In addition, by positioning the plurality of drive motors 20 and the at least one driver 30 within the limited space defined by the first and second frame plates 101 and 102, the electromagnetic shielding performance for the active components can be enhanced. Moreover, since the plurality of drive motors 20 and at least one driver 30 are disposed closely, cable (including power cables, communication cables and/or encoder cables) damage, short circuits, disconnections, communication interruptions and/or excessive cable impedance can be avoided, thus enhancing the control accuracy of the surgical robot and reducing the risk of failure. The requirements of wiring, routing, process, maintenance, heat dissipation and electromagnetic interference avoidance also can be met through the configuration of the plurality of drive motors 20 and at least one driver 30.

In a specific embodiment, as shown in FIG. 1, the at least one driver 30 includes a plurality of single-axis drivers 301. The number of single-axis drivers 301 is the same as the number of drive motors 20, and each single-axis driver 301 is electrically and communicatively connected to one drive motor 20. The plurality of single-axis drivers 301 are electrically and communicatively connected to each other, where the plurality of single-axis drivers 301 and the plurality of drive motors 20 correspond one to one and communicate in series with each other. Although the number of cables is increased to some extent, the limited space defined by the first and second frame plates 101 and 102 can be efficiently utilized according to actual needs, and precise, rapid and/or reliable surgical operations can be achieved under the control of the surgical robot. Moreover, even if a single-axis driver 301 fails, only the faulty single-axis driver 301 needs to be replaced, achieving simple structure and ease of use.

Figure 21:
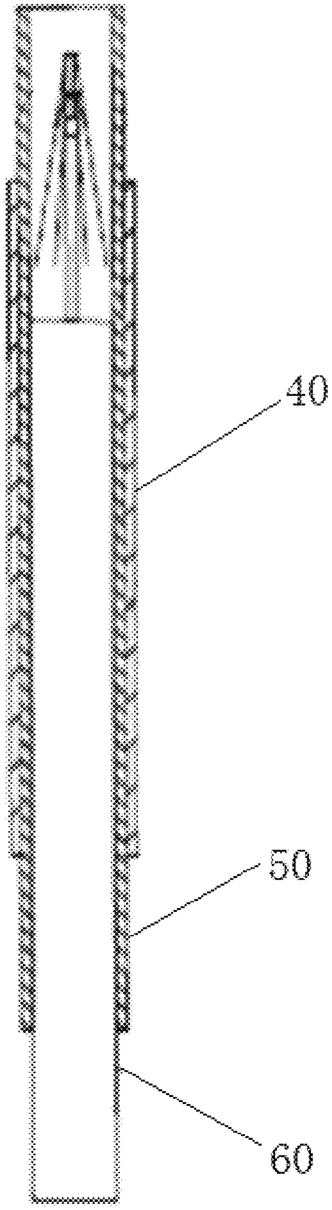
FIG. 21 shows a schematic structural diagram of a specific embodiment of an outer catheter, a middle catheter and an inner catheter according to the present disclosure.

In a specific embodiment, as shown in FIGS. 1 and 21, the number of single-axis drivers 301 and the number of drive motors 20 are both twelve, where the number of single-axis drivers 301 and drive motors 20 can be set according to actual needs. For example, for displacement, rotation and/or steering operations of the outer catheter 40 in the surgical robotic actuation device, three drive motors 20 are required to drive the respective operations; for displacement and/or bi-directional steering operations of the middle catheter 50 in the surgical robotic actuation device, two drive motors 20 are required to drive the respective operations; and for operations of the inner catheter 60 in the surgical robotic actuation device that include axial displacement of the handle, axial rotation of the handle, control of the locking rod, control of the lifting and capturing of the capture arm, and/or control of the opening or closing of the large arm of the implant clamp, six drive motors 20 are required to drive the respective operations.

In a specific embodiment, as shown in FIGS. 2, 7, 12, and 16, the at least one driver 30 includes a first multi-axis driver 302, a second multi-axis driver 303, and a third multi-axis driver 304. Each of the first, second and third multi-axis drivers 302, 303 and 304 is electrically and communicatively connected to more than one drive motor 20. The first, second and third multi-axis drivers 302, 303 and 304 are electrically and communicatively connected to each other. By the first multi-axis driver 302, the second multi-axis driver 303 and the third multi-axis driver 304 each electrically and communicatively connected to more than one drive motor 20, the number of cables can be reduced and meet the actual needs. In a specific embodiment, as shown in FIGS. 2, 7, 12, 16 and 21, the first multi-axis driver 302 is electrically and communicatively connected to three drive motors 20, which can meet the actual needs. The second multi-axis driver 303 is electrically and communicatively connected to another three drive motors 20, which can meet the actual needs. The third multi-axis driver 304 is electrically and communicatively connected to six drive motors 20, which can meet the actual needs. For example, the first multi-axis driver 302 is electrically and communicatively connected to three drive motors 20, which can meet the needs of the outer catheter 40 in the surgical robotic actuation device to displace, rotate and/or steer. The second multi-axis driver 303 is electrically and communicatively connected to three drive motors 20, which can meet the needs of the middle catheter 50 in the surgical robotic actuation device to displace and/or perform bi-directional steering operations. The third multi-axis driver 304 is electrically and communicatively connected to six drive motors 20, which can meet the needs of the inner catheter 60 in the surgical robotic actuation device for axial displacement of the handle, axial rotation of the handle, control of the locking rod, control of the lifting and capturing of the capture arm, and/or control of the opening or closing of the large arm of the implant clamp.

Figure 2:
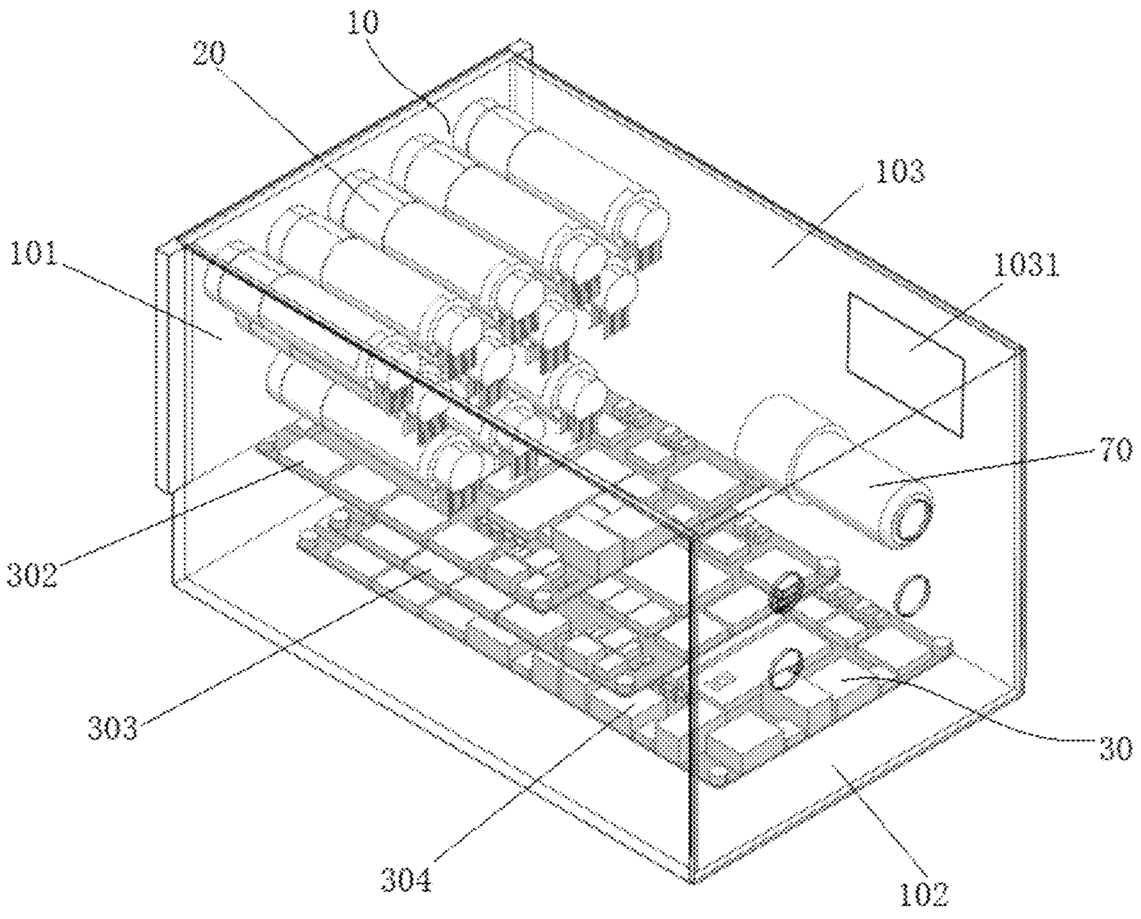
FIG. 2 shows a schematic structural diagram of a specific embodiment of the drive apparatus for surgical robot according to the present disclosure.

In a specific embodiment, as shown in FIG. 2, the first, second and third multi-axis drivers 302, 303 and 304 are disposed within the assembly frame 10 in a three-layer configuration of upper, middle, and lower layers, which can save space.

Figure 7:
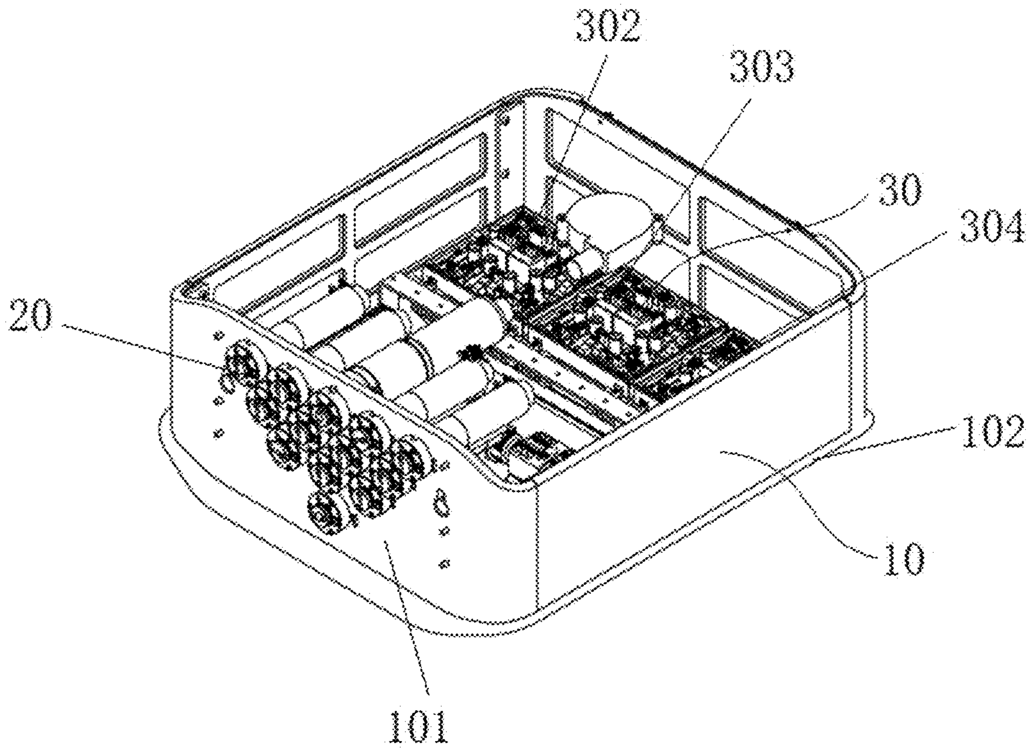
FIG. 7 shows a schematic structural diagram of a specific embodiment of the drive apparatus for surgical robot according to the present disclosure.
Figure 12:
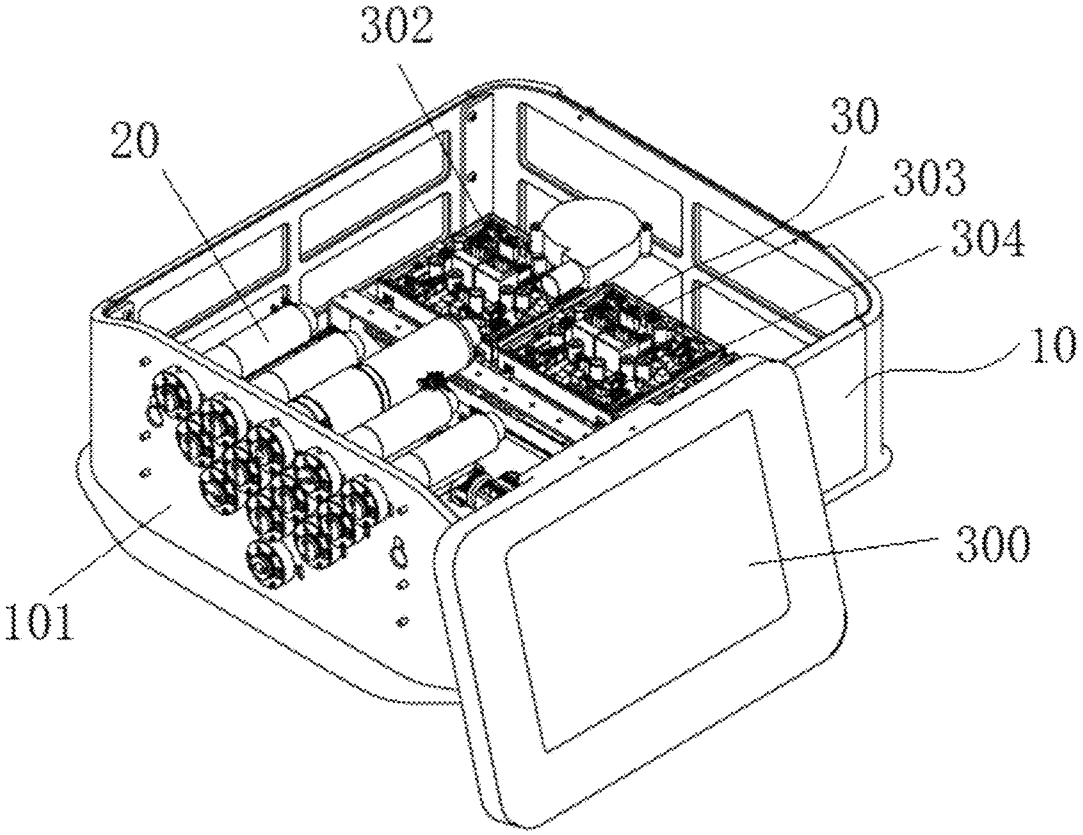
FIG. 12 shows a schematic structural diagram of a specific embodiment of the drive apparatus for surgical robot according to the present disclosure with a display screen provided on the side.
Figure 16:
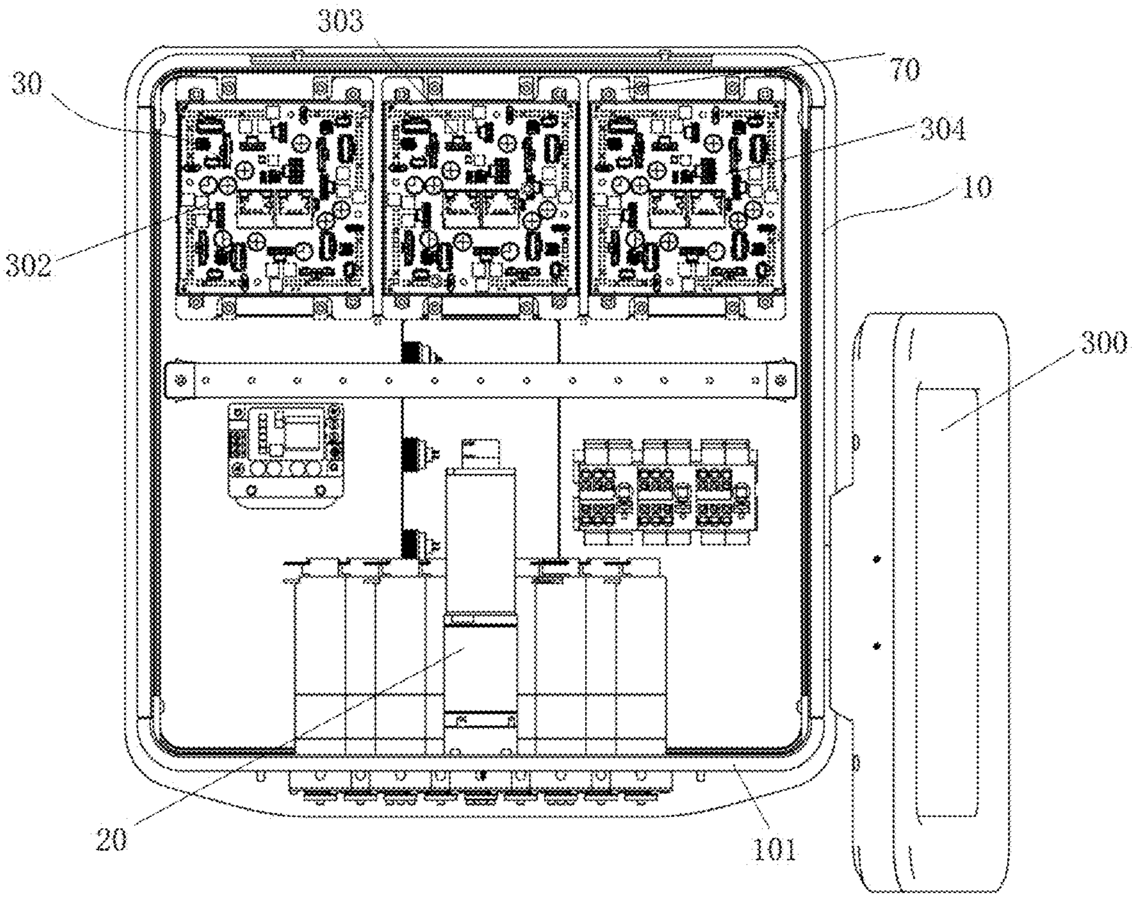
FIG. 16 shows a schematic structural diagram of a specific embodiment of the drive apparatus for surgical robot according to the present disclosure with an external encoder provided on the drive motor.

In a specific embodiment, as shown in FIGS. 7, 12, and 16, the first, second and third multi-axis drivers 302, 303 and 304 are arranged in a row on the second frame plate 102, achieving higher compactness of the layout and ease of use.

In a specific embodiment, as shown in FIGS. 1, 2, and 16, the drive apparatus further includes a heat dissipation unit 70 disposed near a peripheral edge within the assembly frame 10 and configured to expel the heat generated by the operation of at least one driver 30 and/or the plurality of drive motors 20 in the drive apparatus from the surgical robotic actuation device, and draw in the purified cold air from the operating room through the mechanical arm or the mechanical arm base, thereby facilitating the heat exchange.

In a specific embodiment, as shown in FIGS. 1, 2 and 16, the heat dissipation unit 70 includes a cooling fan, a piston air pump, and/or a blower, enabling effective heat dissipation, a simple structure, and ease of use.

In a specific embodiment, as shown in FIGS. 1 and 2, the assembly frame 10 includes a third frame plate 103. The third frame plate 103 is fixedly connected to the first and second frame plates 101 and 102. The third frame plate 103 has an opening portion 1031 formed thereon. The opening portion 1031 includes a mechanical arm interface, a power interface, a communication interface, and an air convection interface, where the mechanical arm interface is configured for connection to the mechanical arm, the power interface is configured for supplying power to at least one driver 30, the plurality of drive motors 20 and/or the heat dissipation unit 70, the communication interface is configured for providing communication signals to at least one driver 30, the plurality of drive motors 20 and/or the heat dissipation unit 70, and the air convection interface is configured for providing ventilation and heat dissipation support for at least one driver 30, the plurality of drive motors 20 and/or the heat dissipation unit 70.

In a specific embodiment, as shown in FIGS. 11 to 16, the drive apparatus further includes a display screen 300. The display screen 300 is mounted on the exterior side of the assembly frame 10, facilitating the display of relevant information and enables convenient touch operations. The display screen 300 is a bedside touchscreen mounted on the side close to the operating bed.

Figure 17:
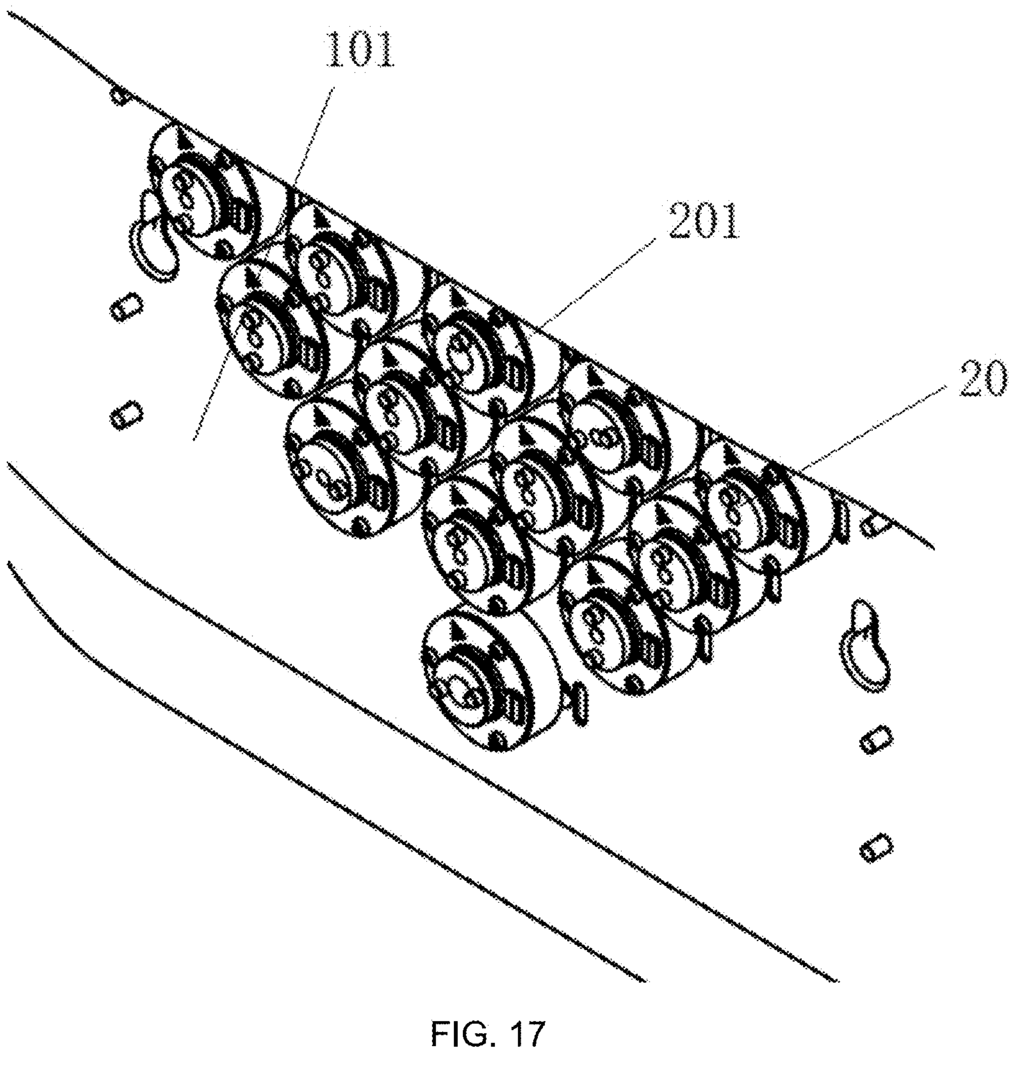
FIG. 17 shows a schematic structural diagram of a specific embodiment of the drive apparatus for surgical robot according to the present disclosure with a display screen provided on the side.

In a specific embodiment, as shown in FIG. 17, each drive motor 20 is provided with an external encoder 201 (an encoder outside the motor 20, e.g., a second encoder) on its output shaft, which can prevent uncontrolled motor operation (runaway) caused by damage to the original encoder (e.g., first encoder) of the motor 20 and can compensate for the lack of multi-turn feedback function of the original encoder of the motor 20, enabling precise multi-turn control. Each of the first and second encoders may be either incremental encoder or absolute encoder.

In a specific embodiment, as shown in FIGS. 1, 2, and 5 to 17, the at least one driver 30 receives a position value fed back from the external encoder 201 of each drive motor 20 and then performs internal closed-loop algorithm calculations to control the respective output powers of the drive motors 20, enabling precise control over the speeds, positions, torques, start/stop, and/or holding functions of the drive motors 20, thus achieving high control accuracy and reliability.

In a specific embodiment, the controller is provided with a hold key and/or a reset key, where the hold key has the function of causing the device to maintain the current position and record it, and the reset key has the function of returning the device to the initial position with a single press.

In a specific embodiment, as shown in FIGS. 1, 2, and 5 to 17, each drive motor 20 is provided with a constant speed mode motion key, a position mode motion key, and/or a constant torque mode motion key, allowing selection based on actual needs. Each drive motor 20 can operate in constant speed mode motion, position mode motion or constant torque mode motion, achieving convenience and efficiency.

In a specific embodiment, as shown in FIGS. 1, 2, and 5 to 17, each drive motor 20 is provided with a safety torque off button, which enables the immediate shutdown of output torque in emergency situations, thus enhancing the safety of the drive motor 20 operation.

In a specific embodiment, as shown in FIGS. 1, 2, 7, 10, 12, 15, and 16, the controller is electrically connected to at least one driver 30 and establishes EtherCAT (Ethernet control automation technology) communication, CANOpen (industrial communication protocol) communication, Profinet (a new generation of automation bus standard based on industrial Ethernet technology) communication or serial port protocol communication. Control and feedback acquisition are performed with the real-time synchronization speed down to the microsecond and even nanosecond level that is achieved by EtherCAT, thereby ensuring high control accuracy and reliability.

Figure 8:
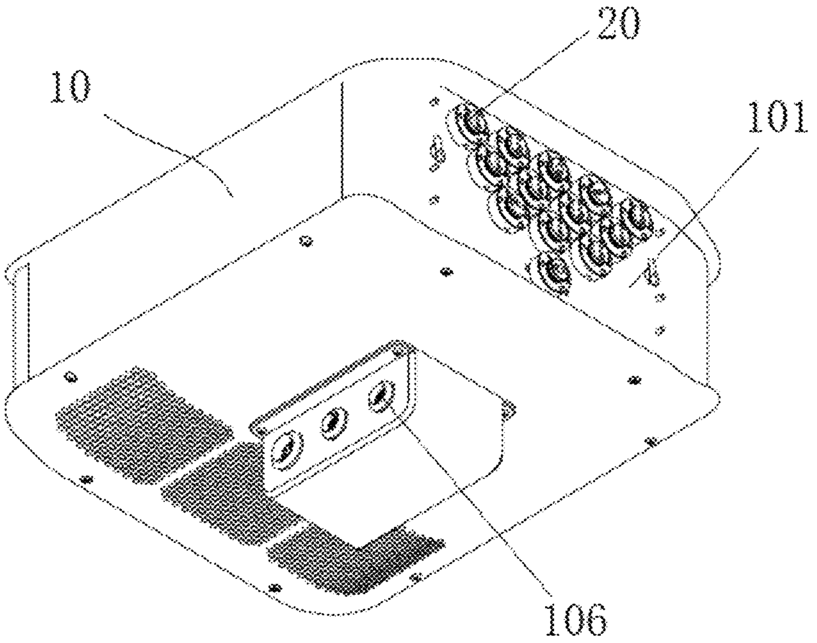
FIG. 8 shows a schematic structural diagram of a specific embodiment of the drive apparatus for surgical robot according to the present disclosure.
Figure 9:
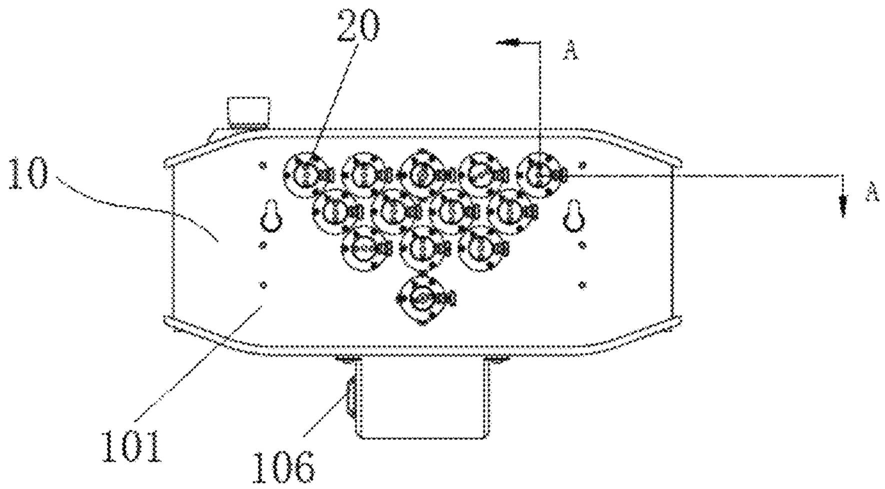
FIG. 9 shows a schematic structural diagram of a specific embodiment of the drive apparatus for surgical robot according to the present disclosure.
Figure 10:
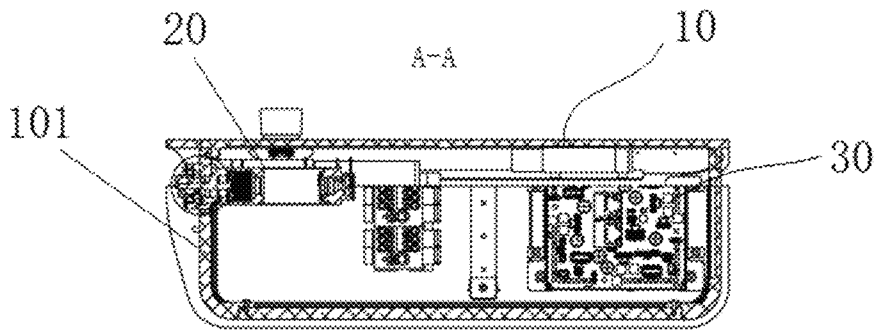
FIG. 10 shows a schematic cross-sectional view of FIG. 9 along the A-A direction.
Figure 11:
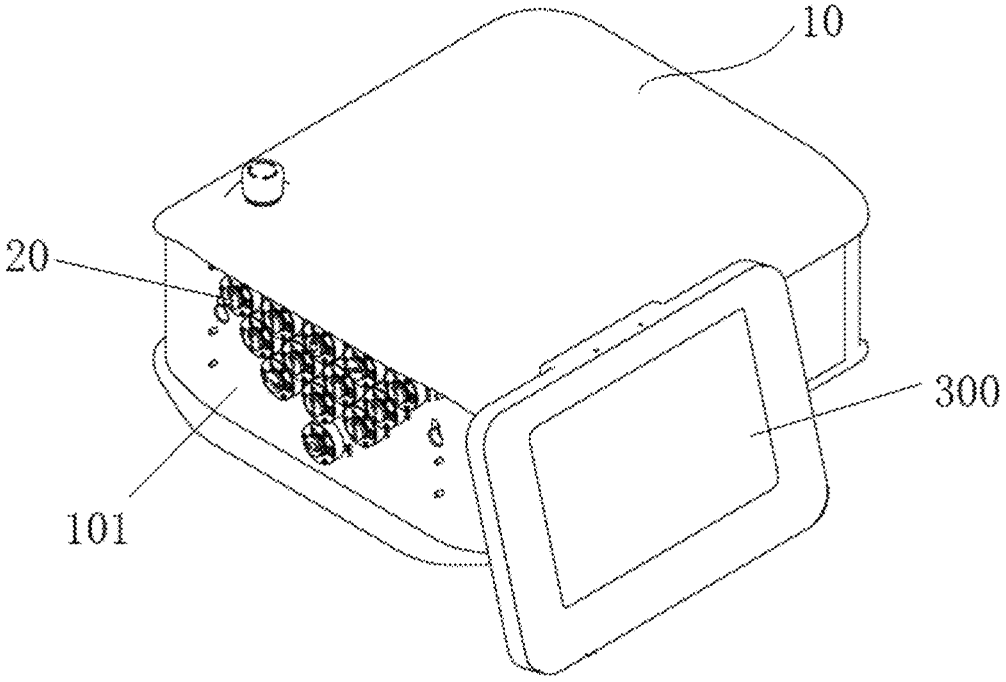
FIG. 11 shows a schematic structural diagram of a specific embodiment of the drive apparatus for surgical robot according to the present disclosure with a display screen provided on the side.
Figure 13:
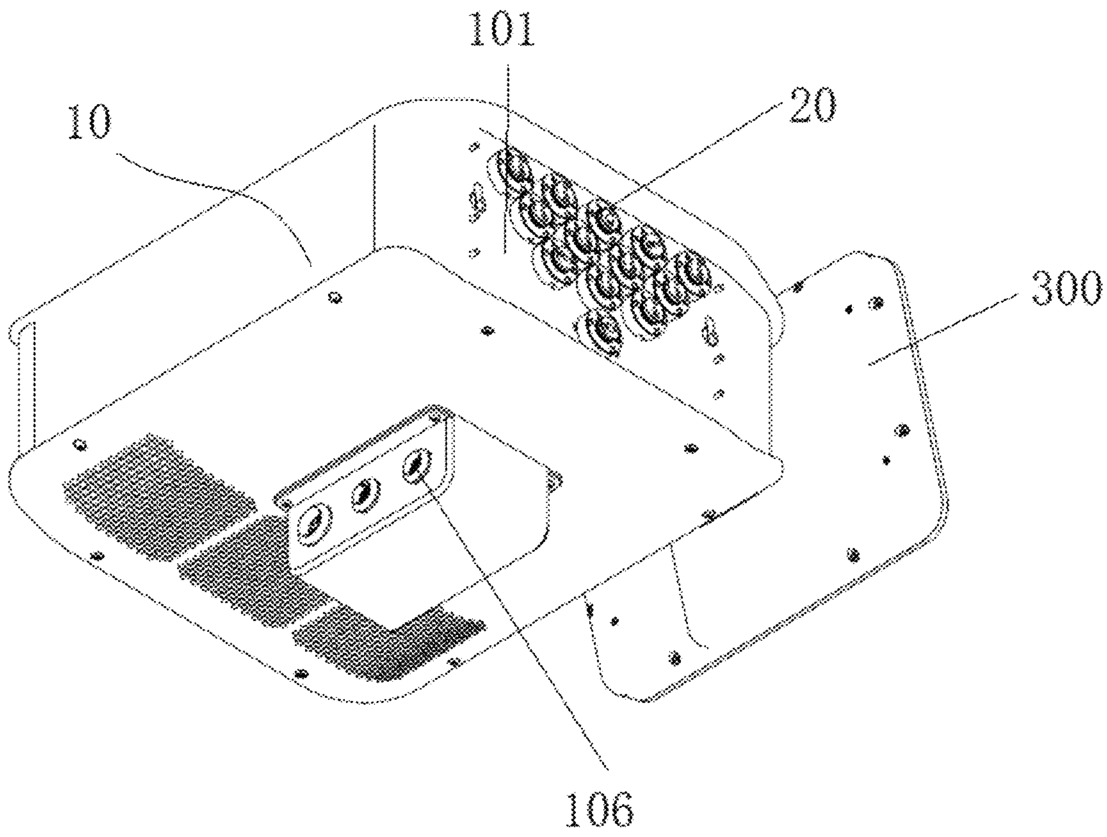
FIG. 13 shows a schematic structural diagram of a specific embodiment of the drive apparatus for surgical robot according to the present disclosure with a display screen provided on the side.
Figure 14:
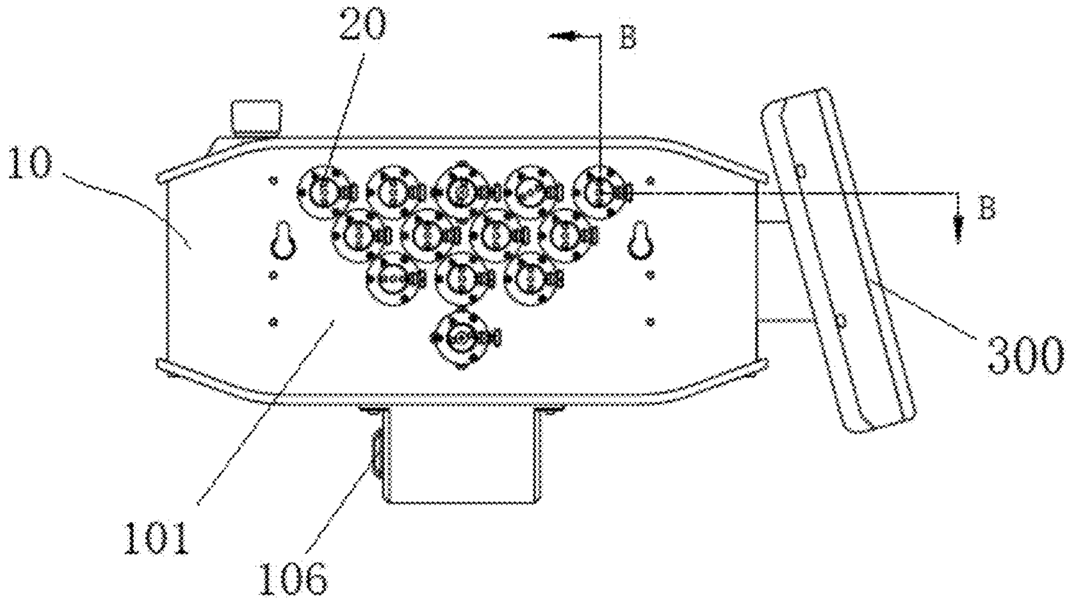
FIG. 14 shows a schematic structural diagram of a specific embodiment of the drive apparatus for surgical robot according to the present disclosure with a display screen provided on the side.
Figure 15:
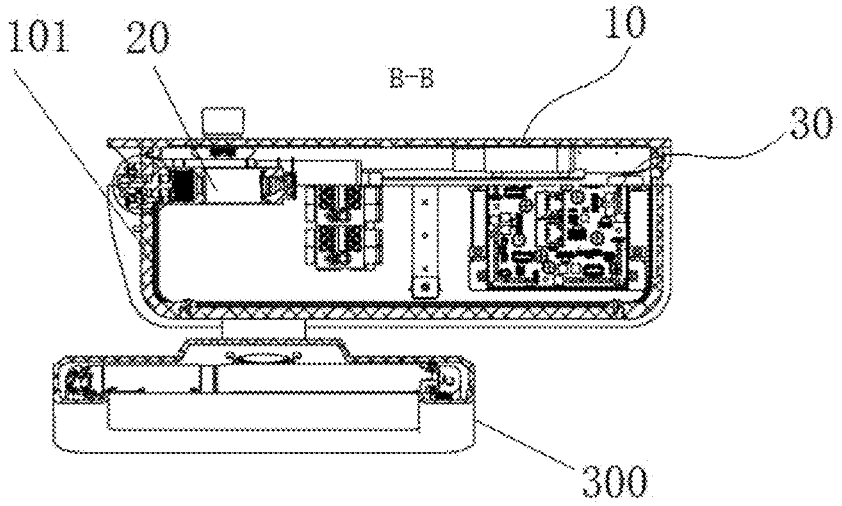
FIG. 15 shows a schematic cross-sectional view of FIG. 14 along the B-B direction.

In a specific embodiment, the drive apparatus is provided in the surgical robotic actuation device and connected to the mechanical arm of the surgical robot through a power cable and a communication cable. As an example, as shown in FIGS. 8 and 13, the drive apparatus is connected to the mechanical arm through a plurality of connector holes 106 on the bottom terminal box of the assembly frame 10.

In a specific embodiment, as shown in FIGS. 1, 2, and 5 to 17, each drive motor 20 is a servo motor having a rapid response capability and stable operation characteristic, thereby meeting actual needs, and achieving a simple structure and ease of use.

In a specific embodiment, as shown in FIGS. 1, 2, 7, 10, 12, 15, and 16, at least one driver 30 is a servo driver having rapid response speed, high stability, strong adaptability, and high precision.

In a specific embodiment, as shown in FIGS. 3 to 5, and 18 to 20, the drive apparatus for surgical robot includes a motor assembly 80 having an assembly frame 10 and a plurality of drive motors 20 mounted thereon (as shown in FIGS. 1 and 2), where each drive motor 20 has an output end that extends through the assembly frame 10 for a coaxial detachable connection to an input end connection assembly 901 of a transmission cabin 90 of the surgical robot. The number of drive motors 20 is the same as the number of input end connection assemblies 901. The drive apparatus is in transmission connection with the transmission cabin 90, where the drive apparatus is configured to generate power, and the transmission cabin 90 is configured to transmit power. Through the split design of the drive apparatus and the transmission cabin 90, the active and passive components of the actuation device can be separated, which eliminates the risk of cable breakage or wear during transmission and movement of the actuation device, thereby avoiding the issue of active connectors loosening due to long-term operation, and improving the electromagnetic shielding performance for the active components by isolating them within the drive apparatus. In addition, the design matching the output ends of the drive motors 20 with the input end connection assemblies 901 ensures smooth transmission between the drive apparatus and the transmission cabin 90 and facilitates the modular design of the drive apparatus and the transmission cabin 90, thereby enhancing the flexibility of the actuation device in use, thus facilitating its application to a broader range of surgical procedures.

Figure 3:
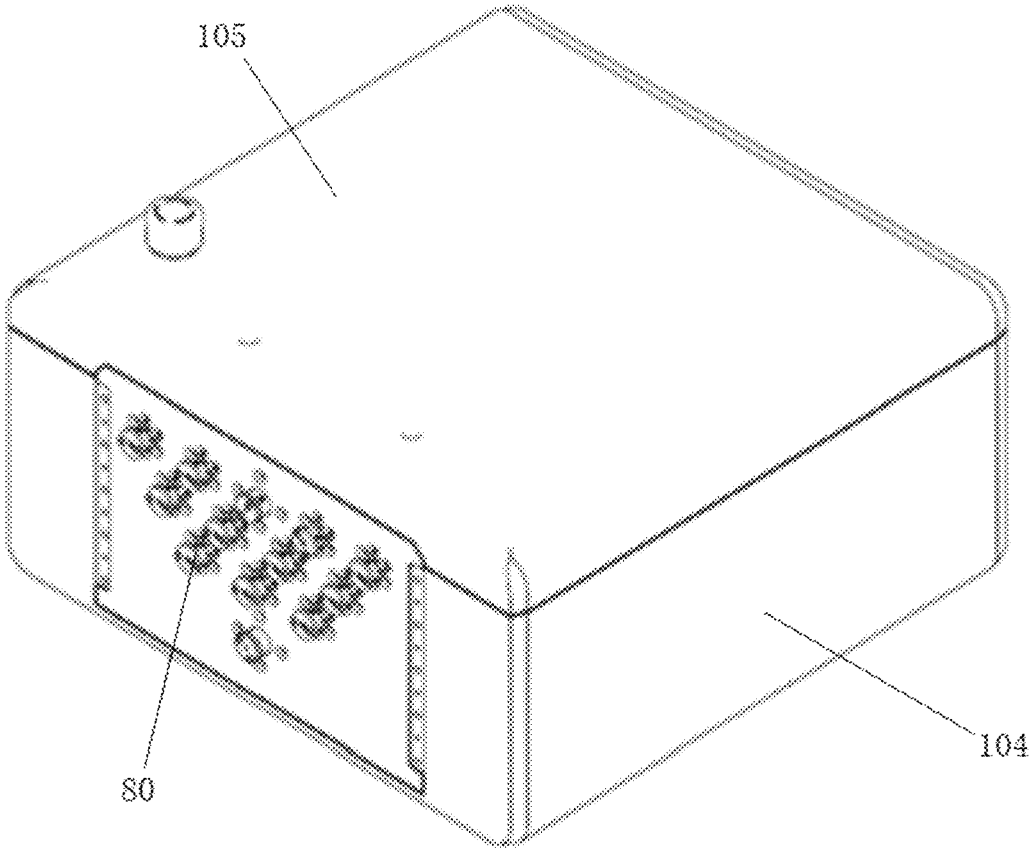
FIG. 3 shows a schematic structural diagram of a specific embodiment of the drive apparatus for surgical robot according to the present disclosure.
Figure 4:
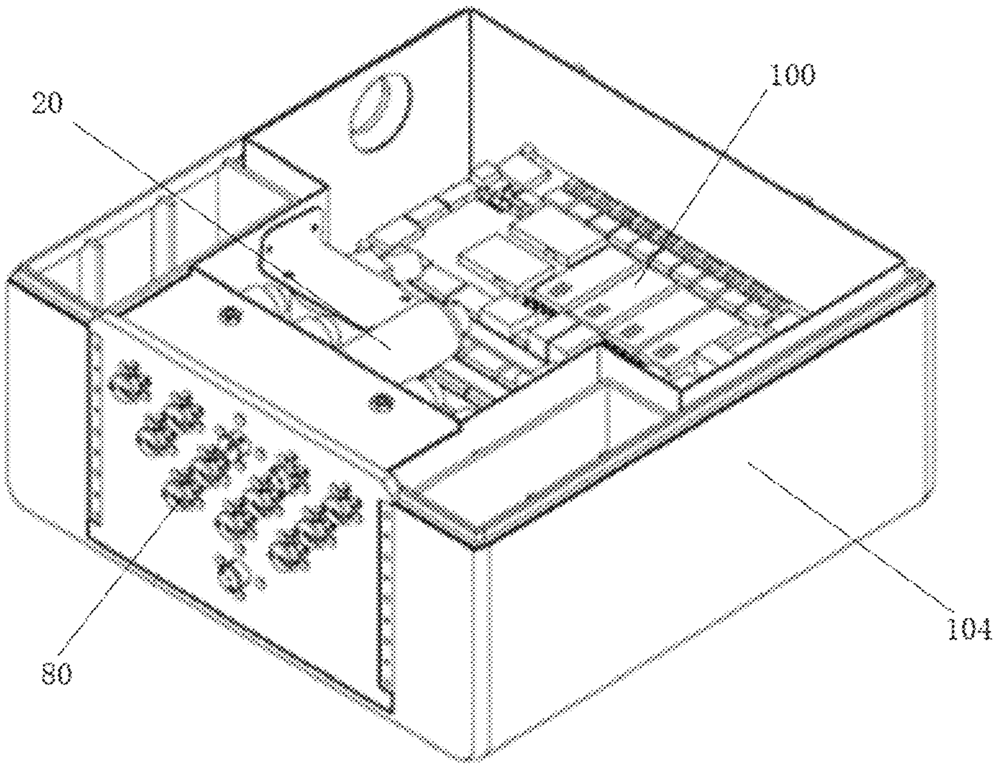
FIG. 4 shows a schematic structural diagram of a specific embodiment of the drive apparatus for surgical robot according to the present disclosure.

In a specific embodiment, as shown in FIGS. 3 to 5, the drive apparatus further includes a bottom shell 104 and a top cover 105 that is buckled on the top of the bottom shell 104. The bottom shell 104 and the top cover 105 together form an accommodation space, in which the driver assembly 100 and all the drive motors 20 are installed. The driver assembly 100 is communicatively connected to the motor assembly 80.

Figure 18:
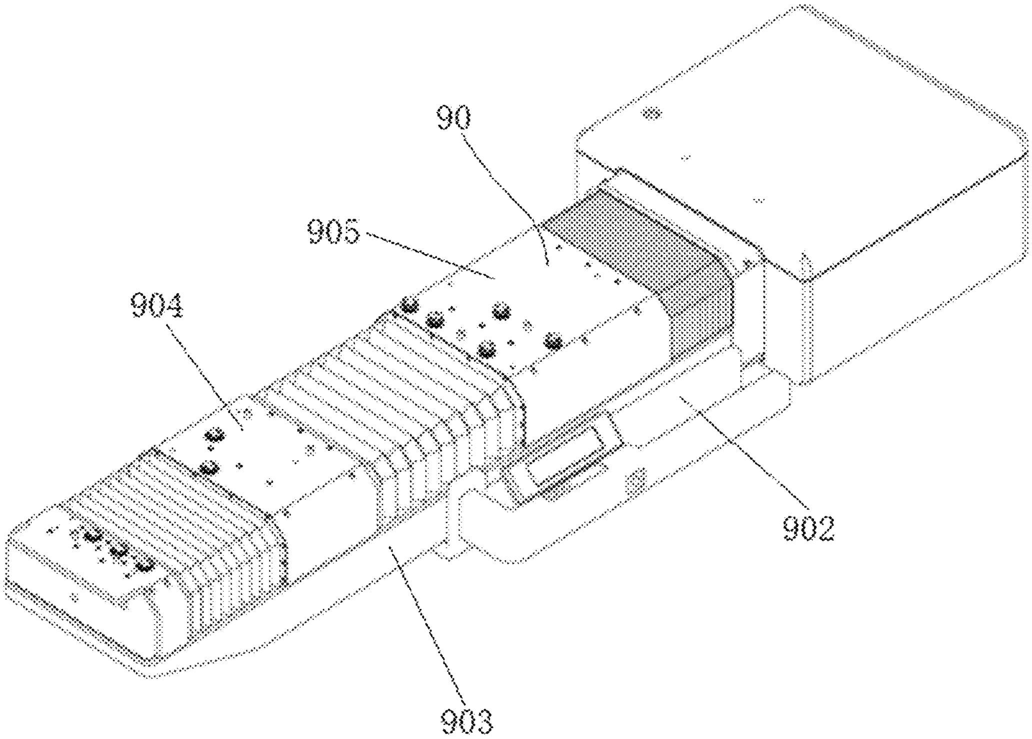
FIG. 18 shows a schematic structural diagram of a specific embodiment of the drive apparatus for surgical robot according to the present disclosure with a transmission cabin connected thereto.
Figure 19:
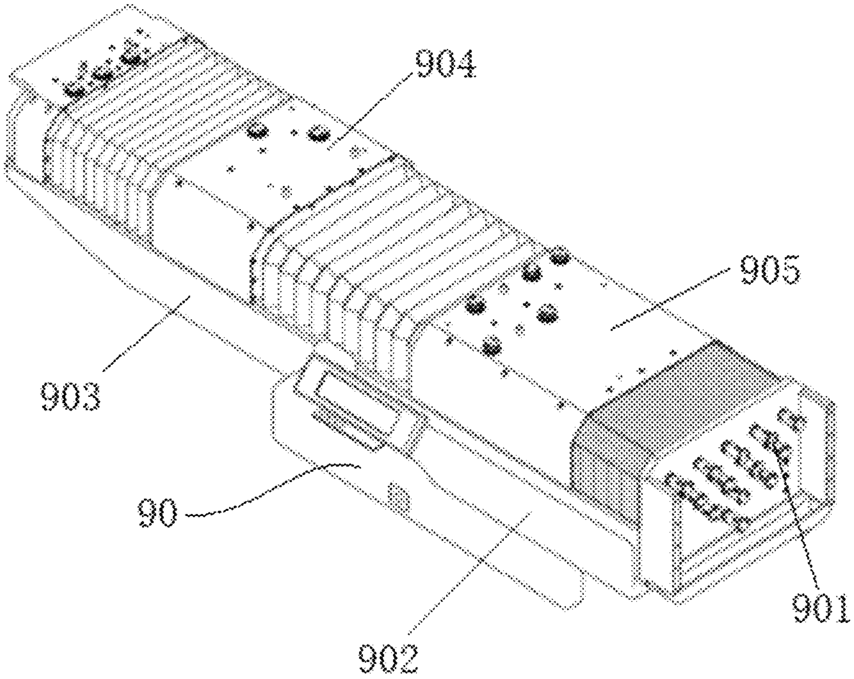
FIG. 19 shows a schematic structural diagram of a specific embodiment of a transmission cabin of the present disclosure.
Figure 20:
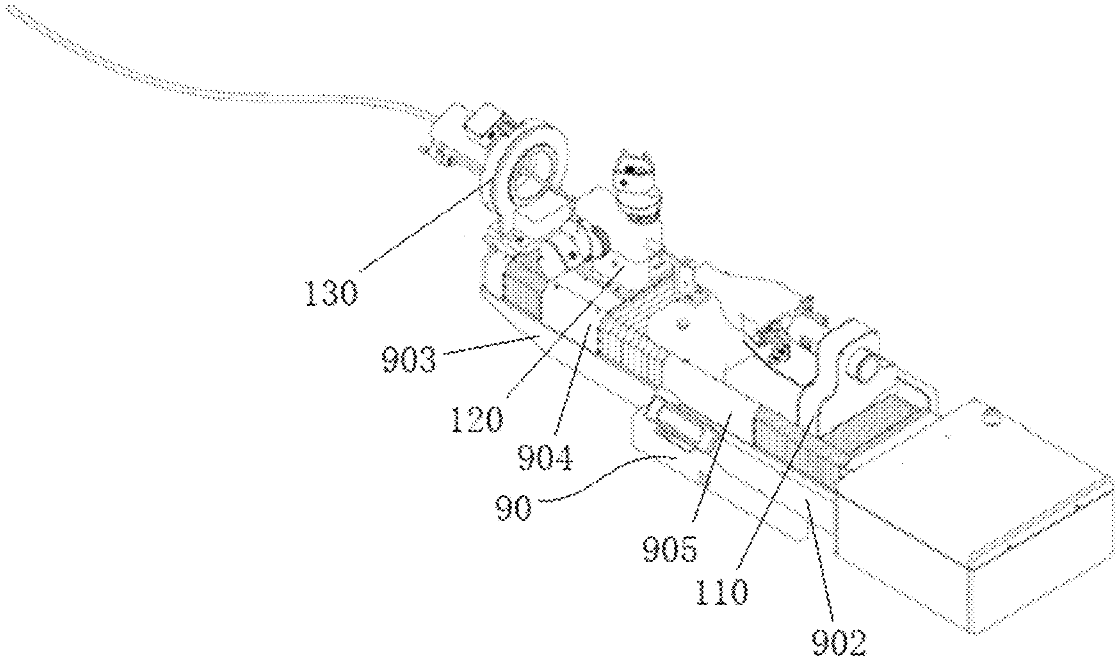
FIG. 20 shows a schematic structural diagram of another specific embodiment of the drive apparatus for surgical robot according to the present disclosure with a transmission cabin connected thereto.

In a specific embodiment, as shown in FIGS. 18 to 20, the transmission cabin 90 includes a chassis assembly 902, and further includes a first adapter transmission assembly 903, a second adapter transmission assembly 904 and a third adapter transmission assembly 905 that are movable relative to the chassis assembly 902. The first adapter transmission assembly 903 includes a first transmission module detachably connected to the first adapter assembly 110. The second adapter transmission assembly 904 includes a second transmission module detachably connected to the second adapter assembly 120. The third adapter transmission assembly 905 includes a third transmission module detachably connected to the third adapter assembly 130. The drive apparatus drives the first adapter assembly 110 through the first transmission module, thereby enabling the first adapter assembly 110 to complete predetermined operations. The drive apparatus drives the second adapter assembly 120 through the second transmission module, thereby enabling the second adapter assembly 120 to complete predetermined operations. The drive apparatus drives the third adapter assembly 130 through the third transmission module, thereby enabling the third adapter assembly 130 to complete predetermined operations. In addition, the first, second and third adapter transmission assemblies 903, 904 and 905 are all driven by motors, thereby enabling precise control over speed, position and even force output as required. Moreover, the highly flexible structure as above allows for replacement of different adapter transmission assemblies within the transmission cabin 90 as required, thereby meeting various surgical procedures.

In a specific embodiment, the surgical robot is an interventional surgical robot that can meet actual needs.

In a specific embodiment, as shown in FIGS. 20 and 21, the first adapter assembly 110 is configured to connect to the outer catheter 40. The second adapter assembly 120 is configured to connect to the middle catheter 50. The third adapter assembly 130 is configured to connect to the output end of the inner catheter 60. The outer catheter 40 is actuated through the first adapter assembly 110 by the drive apparatus to execute corresponding motions. The middle catheter 50 is actuated through the second adapter assembly 120 by the drive apparatus to execute corresponding motions. The inner catheter 60 is actuated through the third adapter assembly 130 by the drive apparatus to execute corresponding motions. The design which involves actuating the outer catheter 40, the middle catheter 50 and the inner catheter 60 separately enhances the flexibility of the mitral valve repair instrument and facilitates refined operations thereof. Utilizing the aforesaid actuation device for valve repair surgeries can further ensure the stability and accuracy of the procedures. The actuation device actuates the first, second and third adapter assemblies 110, 120 and 130 individually, which enhances the flexibility of the motions output by these adapter assemblies, thereby facilitating refined operations required for the surgical procedures, thus ensuring that the actuation device operates with greater precision, stability and safety.

In the drive apparatus for surgical robot according to the present disclosure, since the plurality of drive motors 20 are mounted on the first frame plate 101 and the at least one driver 30 is mounted on the second frame plate 102, the plurality of drive motors 20 and at least one driver 30 can be located in close proximity, so that the plurality of drive motors 20 and at least one driver 30 can be placed in the limited space defined by the first and second frame plates 101 and 102, thereby enabling the configuration of the plurality of drive motors 20 and at least one driver 30 within the space-constrained surgical robotic actuation device. Either the simple movement of the single-axis driver 301, or the synchronized, reciprocating (fly-saw) and/or tension-compensation motions of the first, second and third multi-axis drivers 302, 303 and 304 enable the plurality of drive motors 20 to achieve the required real-time motion performance, thereby allowing the surgeons to perform precise, rapid and/or reliable surgical operations by controlling the interventional surgical robot. In addition, when in use, the drive apparatus for surgical robot is installed on the right side of the transmission cabin 90. The chassis assembly 902 is located at the bottom of the transmission cabin 90, the first adapter transmission assembly 903 is installed above the chassis assembly 902, the second adapter transmission assembly 904 is installed above the first adapter transmission assembly 903, the third adapter transmission assembly 905 is installed on the right side of the second adapter transmission assembly 904, and the axial end fixing assembly 906 is provided on the right side of the transmission cabin 90. The axial end fixing assembly 906 can be quickly coupled to the motor assembly 80, enabling rapid attachment and detachment of the transmission cabin 90 to the drive apparatus.

Based on the above embodiments, the present disclosure further proposes a surgical robot including the aforesaid drive apparatus for surgical robot. The drive apparatus allows the surgeons to perform precise, rapid and/or reliable surgical operations by controlling the surgical robot.

The scope of protection of the present disclosure is not limited to the above embodiments. It is evident that a person of ordinary skill in the art can make various changes or modifications to the present disclosure without departing from the scope and spirit of the present disclosure. Any change and modification made within the scope of the claims of the present disclosure and their equivalent technologies are intended to be encompassed within the present disclosure.

What is claimed is:

1. A drive apparatus for surgical robot, comprising
- an assembly frame (10),
- a plurality of drive motors (20),
- at least one driver (30), and
- a controller, wherein
- the assembly frame (10) comprises a first frame plate (101) and a second frame plate (102) that is fixedly connected to the first frame plate (101);
- each of the plurality of drive motors (20) is mounted on the first frame plate (101) and has a power output end that extends outwardly through the first frame plate (101) for connecting to and providing driving power for an external device; and
- the at least one driver (30) is mounted on the second frame plate (102) and connected electrically and communicatively to the controller and the plurality of drive motors (20), and is configured to cause, according to instructions of the controller, the plurality of drive motors (20) to output respective powers for providing a plurality of driving powers for the external device.

2. The drive apparatus for surgical robot according to claim 1, wherein the at least one driver (30) comprises a plurality of single-axis drivers (301), the number of the single-axis drivers (301) being the same as the number of the drive motors (20), each of the single-axis drivers (301) being electrically and communicatively connected to one of the drive motors (20), and the plurality of single-axis drivers (301) being electrically and communicatively connected to each other.

3. The drive apparatus for surgical robot according to claim 2, wherein the number of the single-axis drivers (301) and the number of the drive motors (20) are both twelve.

4. The drive apparatus for surgical robot according to claim 1, wherein the at least one driver (30) comprises a first multi-axis driver (302), a second multi-axis driver (303) and a third multi-axis driver (304) each being electrically and communicatively connected to more than one of the drive motors (20), the first multi-axis driver (302), the second multi-axis driver (303) and the third multi-axis driver (304) being electrically and communicatively connected to each other.

5. The drive apparatus for surgical robot according to claim 4, wherein the first multi-axis driver (302) is electrically and communicatively connected to three of the drive motors (20), the second multi-axis driver (303) is electrically and communicatively connected to another three of the drive motors (20), and the third multi-axis driver (304) is electrically and communicatively connected to six of the drive motors (20).

6. The drive apparatus for surgical robot according to claim 4, wherein the first multi-axis driver (302), the second multi-axis driver (303) and the third multi-axis driver (304) are disposed within the assembly frame (10) in a three-layer configuration of upper, middle, and lower layers.

7. The drive apparatus for surgical robot according to claim 1, wherein the assembly frame (10) comprises a third frame plate (103) fixedly connected to the first frame plate (101) and the second frame plate (102), the third frame plate (103) having an opening (1031) that comprises a mechanical arm interface, a power interface, a communication interface and an air convection interface.

8. The drive apparatus for surgical robot according to claim 1, further comprising a heat dissipation unit (70) disposed within the assembly frame (10) near a peripheral edge.

9. The drive apparatus for surgical robot according to claim 8, wherein the heat dissipation unit (70) comprises a cooling fan, a piston air pump, and/or a blower.

10. The drive apparatus for surgical robot according to claim 1, wherein the controller is provided with a hold key and/or a reset key.

11. The drive apparatus for surgical robot according to claim 1, wherein each of the drive motors (20) is provided with a constant speed mode motion key, a position mode motion key, and/or a constant torque mode motion key.

12. The drive apparatus for surgical robot according to claim 1, wherein each of the drive motors (20) is provided with a safety torque off key.

13. The drive apparatus for surgical robot according to claim 1, wherein each of the drive motors (20) has an output shaft with an external encoder (201) provided thereon.

14. The drive apparatus for surgical robot according to claim 1, wherein the drive apparatus is disposed in a surgical robotic actuation device and is connected to a mechanical arm of the surgical robot through a power cable and a communication cable.

15. A surgical robot, comprising
- a drive apparatus for surgical robot that comprises
  - an assembly frame (10),
  - a plurality of drive motors (20),
  - at least one driver (30), and a controller, wherein the assembly frame (10) comprises a first frame plate (101) and a second frame plate (102) that is fixedly connected to the first frame plate (101);

each of the plurality of drive motors (20) is mounted on the first frame plate (101) and has a power output end that extends outwardly through the first frame plate (101) for connecting to and providing driving power for an external device; and the at least one driver (30) is mounted on the second frame plate (102) and connected electrically and communicatively to the controller and the plurality of drive motors (20), and is configured to cause, according to instructions of the controller, the plurality of drive motors (20) to output respective powers for providing a plurality of driving powers for the external device.

16. The surgical robot according to claim 15, wherein the at least one driver (30) comprises a plurality of single-axis drivers (301), the number of the single-axis drivers (301) being the same as the number of the drive motors (20), each of the single-axis drivers (301) being electrically and communicatively connected to one of the drive motors (20), and the plurality of single-axis drivers (301) being electrically and communicatively connected to each other.

17. The surgical robot according to claim 16, wherein the number of the single-axis drivers (301) and the number of the drive motors (20) are both twelve.

18. The surgical robot according to claim 15, wherein the at least one driver (30) comprises a first multi-axis driver (302), a second multi-axis driver (303) and a third multi-axis driver (304) each being electrically and communicatively connected to more than one of the drive motors (20), the first multi-axis driver (302), the second multi-axis driver (303) and the third multi-axis driver (304) being electrically and communicatively connected to each other.

19. The surgical robot according to claim 18, wherein the first multi-axis driver (302) is electrically and communicatively connected to three of the drive motors (20), the second multi-axis driver (303) is electrically and communicatively connected to another three of the drive motors (20), and the third multi-axis driver (304) is electrically and communicatively connected to six of the drive motors (20).

20. The surgical robot according to claim 15, wherein each of the drive motors (20) has an output shaft with an external encoder (201) provided thereon.

* * * * *